US007481763B2

(12) United States Patent
Hassler, Jr. et al.

(10) Patent No.: US 7,481,763 B2
(45) Date of Patent: Jan. 27, 2009

(54) METAL BELLOWS POSITION FEEDBACK FOR HYDRAULIC CONTROL OF AN ADJUSTABLE GASTRIC BAND

(75) Inventors: William L. Hassler, Jr., Cincinnati, OH (US); Daniel F. Dlugos, Jr., Morrow, OH (US); Rocco Crivelli, Bellinzona (CH)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 964 days.

(21) Appl. No.: 10/856,971

(22) Filed: May 28, 2004

(65) Prior Publication Data

US 2005/0267500 A1 Dec. 1, 2005

(51) Int. Cl.
*A61F 2/00* (2006.01)
(52) U.S. Cl. ........................................................ 600/37
(58) Field of Classification Search ............. 600/29–32, 600/37, 38; 606/191; 623/23.65–23.67; 604/66, 67, 891.1, 890.1, 544, 132; 128/897, 128/899
See application file for complete search history.

(56) References Cited

U.S. PATENT DOCUMENTS

| 4,505,710 | A |   | 3/1985  | Collins et al. |
|-----------|---|---|---------|----------------|
| 4,581,018 | A |   | 4/1986  | Jassawalla et al. |
| 5,507,737 | A |   | 4/1996  | Palmskog |
| 5,562,598 | A | * | 10/1996 | Whalen et al. ............... 600/29 |
| 5,715,837 | A |   | 2/1998  | Chen |
| 5,733,313 | A |   | 3/1998  | Barreras, Sr. et al. |
| 5,974,873 | A |   | 11/1999 | Nelson |
| 6,058,330 | A |   | 5/2000  | Borza |
| 6,102,678 | A |   | 8/2000  | Peclat |
| 6,315,769 | B1 |  | 11/2001 | Peer et al. |
| 6,327,504 | B1 |  | 12/2001 | Dolgin et al. |
| 6,366,817 | B1 |  | 4/2002  | Kung |
| 6,394,981 | B2 |  | 5/2002  | Heruth |
| 6,416,495 | B1 |  | 7/2002  | Kriesel et al. |
| 6,430,444 | B1 |  | 8/2002  | Borza |
| 6,463,329 | B1 |  | 10/2002 | Goedeke |
| 6,482,177 | B1 |  | 11/2002 | Leinders |
| 6,485,462 | B1 |  | 11/2002 | Kriesel et al. |
| 6,542,350 | B1 |  | 4/2003  | Rogers |
| 2004/0260233 | A1 | * | 12/2004 | Garibotto et al. .............. 604/66 |

FOREIGN PATENT DOCUMENTS

| WO | WO 00 72899 | 12/2000 |
|----|-------------|---------|
| WO | WO 01/12078 | 2/2001  |
| WO | WO 01/49245 | 7/2001  |

* cited by examiner

*Primary Examiner*—Charles A Marmor, II
*Assistant Examiner*—Christine D Hopkins
(74) *Attorney, Agent, or Firm*—Frost Brown Todd LLC (57) ABSTRACT

A remotely controlled gastric band system that is practically immune to external magnetic fields, such as from a Magnetic Resonance Imaging (MRI) machine, incorporates a bi-directional pump and fluid reservoir to adjust fluid volume for hydraulic control of a gastric band. A piezoelectric driver (e.g., rotary actuator, linear actuator) selectively compresses and expands a metal bellows hermetically sealed within a biocompatible and nonferromagnetic enclosure or case such as titanium. Directly sensing a position of the metal bellows yields an accurate reading of volume contained therein, allowing for closed-loop control of the gastric band.

12 Claims, 6 Drawing Sheets

METAL BELLOWS POSITION FEEDBACK FOR HYDRAULIC CONTROL OF AN ADJUSTABLE GASTRIC BAND

CROSS REFERENCE TO RELATED APPLICATIONS

The present application is related to three co-pending and commonly-owned applications filed on even date herewith, the disclosure of each being hereby incorporated by reference in their entirety, entitled respectively:

"PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857762;

"THERMODYNAMICALLY DRIVEN REVERSIBLE INFUSER PUMP FOR USE AS A REMOTELY CONTROLLED GASTRIC BAND" to William L. Hassler, Jr., Daniel F. Dlugos, Jr., Ser. No. 10/857315 ;and "BI-DIRECTIONAL INFUSER PUMP WITH VOLUME BRAKING FOR HYDRAULICALLY CONTROLLING AN ADJUSTABLE GASTRIC BAND" to William L. Hassler, Jr., Daniel F. Dlugos, Jr., Ser. No. 10/857763.

FIELD OF THE INVENTION

The present invention relates, in general, to medically implantable reversible pumps, and more particularly, to such pumps that are suitable for long term use without fluid loss such as for hydraulically controlling an artificial sphincter.

BACKGROUND OF THE INVENTION

An artificial sphincter may be utilized in any number of applications within a patient's body where it is desirable to vary the size of an orifice or organ. Depending upon the application, artificial sphincters may take the form of a flexible, substantially non-extensible band containing an expandable section that is capable of retaining fluids. The expandable section would be capable of expanding or contracting depending upon the volume of fluid contained therein. One particular example of an artificial sphincter is an adjustable gastric banding device, such as described in U.S. Pat. Nos. 4,592,339, 5,226,429, 6,102,922, and 5,449,368, the disclosure of each being hereby incorporated by reference. Since the early 1980s, adjustable gastric bands have provided an effective alternative to gastric bypass and other irreversible surgical weight loss treatments for the morbidly obese.

The gastric band is wrapped around an upper portion of the patient's stomach just inferior to the esophago-gastric junction, forming a stoma that restricts food passing from an upper portion to a lower portion of the stomach. When the stoma is of the appropriate size, food held in the upper portion of the stomach provides a feeling of fullness that discourages overeating. However, initial maladjustment or a change in the stomach over time may lead to a stoma of an inappropriate size, warranting an adjustment of the gastric band. Otherwise, the patient may suffer vomiting attacks and discomfort when the stoma is too small to reasonably pass food. At the other extreme, the stoma may be too large and thus fail to slow food moving from the upper portion of the stomach, defeating the purpose altogether for the gastric band. Thus, different degrees of constriction are desired, and adjustment is required over time as the patient's body adapts to the constriction.

In addition to a latched position to set the outer diameter of the gastric band, adjustability of gastric bands is generally achieved with an inwardly directed inflatable balloon, similar to a blood pressure cuff, into which fluid, such as saline, is injected through a fluid injection port to achieve a desired diameter. Since adjustable gastric bands may remain in the patient for long periods of time, the fluid injection port is typically installed subcutaneously to avoid infection, for instance in front of the sternum or over the fascia covering one of the oblique muscles. Adjusting the amount of fluid in the adjustable gastric band is achieved by inserting a Huber tip needle through the skin into a silicon septum of the injection port. Once the needle is removed, the septum seals against the hole by virtue of compressive load generated by the septum. A flexible catheter communicates between the injection port and the adjustable gastric band.

While the injection port has been successfully used to adjust gastric bands, it would be desirable to make adjustments noninvasively. Insertion of the Huber tip syringe is typically done by a surgeon, which may be inconvenient, painful, or expensive for the patient. In addition, a skin infection may occur at the site of the insertion of the syringe. Consequently, it would be desirable to remotely control an adjustable gastric band.

In an afore-mentioned co-pending application entitled "PIEZO ELECTRICALLY DRIVEN BELLOWS INFUSER FOR HYDRAULICALLY CONTROLLING AN ADJUSTABLE GASTRIC BAND" to William L. Hassler, Jr., Ser. No. 10/857762, an advantageous infuser containing no ferromagnetic materials provides an accurately bi-directionally controllable volume of fluid to a closed gastric band. The infuser has a titanium bellows accumulator, which may be collapsed or extended to positively displace fluid accumulated therein, thereby serving as both a reversible pump and reservoir. Thereby a bi-directional pump that is practically immune to external magnetic fields is achieved, unlike previously known implants that contained a metal bellows for controllable dispensing of a liquid drug, such as described in U.S. Pat. No. 4,581,018. Thereby, such an implanted device may undergo Magnetic Resonance Imaging (MRI) without damage to the device or patient.

Accurate delivery of fluid from a bellows accumulator benefits from a feedback control system and as a means for determining bellows position relative to its housing. In the U.S. Pat. No. 4,581,018 patent, position feedback was provided by a rotary encoder connected to the output shaft of an electrical motor used to rotate the cylindrical metal bellows. In this instance, the rotations of the motor are determined by counting incremental marks on an optical disk of the encoder for the purpose of dispensing at a uniform rate.

However, in creating a device that may be required to pump in both directions with long intervals therebetween, it is believed that counting rotations of a rotary actuator in some instances may inaccurately reflect the volume in the bellows accumulator. For example, the current volume of the reservoir is not directly sensed, and thus integrating a rate of dispensing to calculate a change in volume still suffers if the starting point is not known or if fluid is transferred inadvertently due to leakage or other factors.

In other infuser devices, sensing fluid pressure within the bellows accumulator has been used as an indirect measurement of volume, relying upon a fixed relationship in pressure and volume since the bellows accumulator is collapsed based on a gauge pressure exerted thereon by a propellant within an infuser device housing. However, such pressure sensing assumes that the fluid pressure is not varied by pressure external to the infuser device, such as would be expected in a closed artificial sphincter system. Specifically, the amount of back pressure would vary somewhat unpredictability.

Examples of such pressure-based sensing include U.S. Pat. No. 5,507,737 (pressure gauge), U.S. Pat. No. 5,974,873 (strain gauge), and U.S. Pat. No. 6,315,769 (spring and pressure sensitive resistor).

Recently, it has been recognized as desirable to sense remaining fluid volume in a drug dispensing infuser device in order to determine when refilling is necessary. To that end, U.S. Pat. No. 6,542,350 discloses forming a variable capacitance between the bellows accumulator and the infuser device housing to sense volume. Similarly, U.S. Pat. No. 6,482,177 discloses forming a variable inductance between the bellows accumulator and the infuser device housing to sense volume. In both instances, using the sensed volume for such purposes was not suggested other than relaying a value by telemetry for display to a human operator. This is understandable in that these drug dispensing applications meter small amounts of a drug without significant variations in external backpressure to the infuser. Continuous volume sensing was not addressed. Power consumption for volume sensing would create an undesirable increase in battery size. In addition, accuracy of the variable capacitors or inductors may have been insufficient for these purposes, especially as the portions of the variable capacitor or inductor move away from one another in the presence of electromagnetic interference.

Consequently, a significant need exists for sensing a position of an implanted bellows accumulator representing a fluid volume for closed loop control of an implanted artificial sphincter.

BRIEF SUMMARY OF THE INVENTION

The present invention addresses these and other problems in the prior art by providing volume sensing of a bellows accumulator so that accurate, closed-loop motion control of the bellows accumulator may be achieved.

In one aspect of the invention, a method for hydraulically controlling an implantable artificial sphincter includes a programmer that sends a position signal to an external telemetry coil. The signal is transmitted to an implanted telemetry coil receiver, which delivers it to an implanted microprocessor. The positive control signal then enters a feedback loop-summing junction, which also receives an error signal. The net signal flows to the bellows actuator, which is powered by the secondary transcutaneous energy transfer (TET) coil. A bellows position sensor determines the prior bellows position and an electronic position signal is provided to a control algorithm, which in turn provides the error signal to the summing junction to tell the actuator to move to a new position. Thereby, accurate bi-directional hydraulic control of the artificial sphincter is achieved, even if the rate of fluid dispensing varies due to circumstances such as changing actuation performance or unpredictable back pressure to the infuser device.

In another aspect of the invention, a bi-directional infuser device for an artificial sphincter system incorporates volume sensing for closed-loop adjustment control by control circuitry incorporated into the infuser device. In response to an external programmer command to adjust volume, the control circuitry performs closed loop control of an actuation mechanism with reference to volume sensing until the commanded volume is achieved.

In another aspect of the invention, the bi-directional infuser device is part of an implantable artificial sphincter system that is remotely powered and telemetrically controlled by an external assembly including a primary TET and telemetry coil or coils that advantageously allow noninvasive adjustment of an artificial sphincter, such as a gastric band. Thereby, the need to insert a syringe to adjust volume is avoided, along with the accompanying inconvenience, discomfort and increased likelihood of infection.

These and other objects and advantages of the present invention shall be made apparent from the accompanying drawings and the description thereof.

BRIEF DESCRIPTION OF THE FIGURES

While the specification concludes with claims particularly pointing out and distinctly claiming the present invention, it is believed the same will be better understood by reference to the following description, taken in conjunction with the accompanying drawings in which:

DETAILED DESCRIPTION OF THE INVENTION

Figure 1:
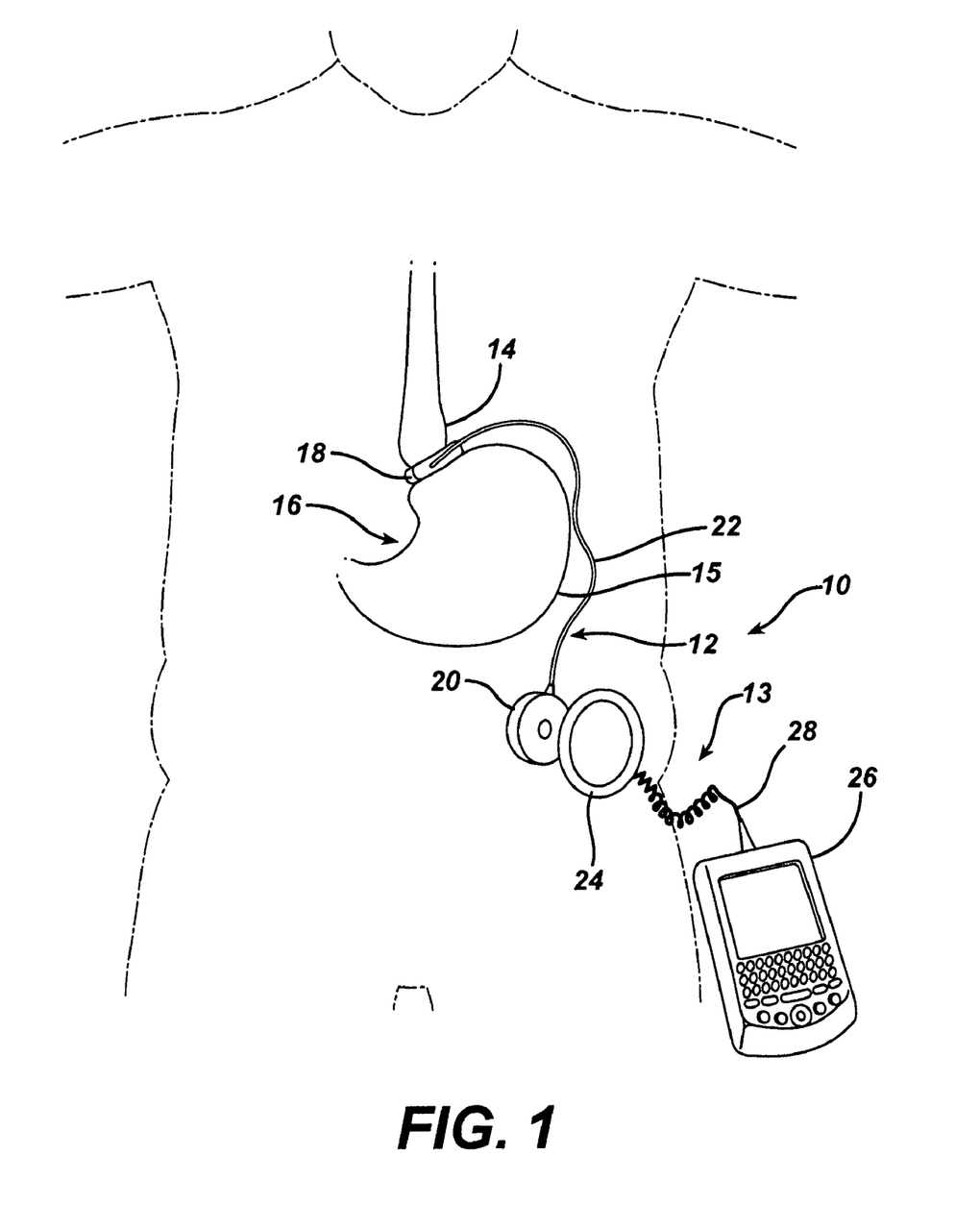
FIG. 1 is a perspective environmental view of an adjustable artificial sphincter system being closed-loop remotely controlled based upon volume sensing.

Turning to the Drawings wherein like numerals denote like components throughout the several views, in FIG. 1, an artificial sphincter system 10 regulates the amount of fluid maintained in an implantable artificial sphincter assembly 12 powered by transcutaneous energy transfer (TET) and under telemetry control of an external assembly 13. In the illustrative version, the artificial sphincter system 10 is used for weight reduction therapy. A stoma is formed between an upper portion 14 and lower portion 15 of a patient's stomach 16 to slow the passage of food and to provide a sense of fullness. The implantable artificial sphincter assembly 12 includes an expandable gastric band 18 that encircles the stomach 16 to form the stoma. An infuser device 20 is anchored subcutaneously on a layer of muscular fascia within the patient or in another convenient location. A flexible catheter 22 provides fluid communication between the gastric band 18 and the infuser device 20.

It should be appreciated that the gastric band 18 includes an inwardly directed bladder to expandably receive a fluid, such as saline solution, from the catheter 22 to allow adjustment of the size of the stoma formed therein without having to adjust the attachment of the gastric band 18. The infuser device 20 advantageously prevents fluid moving in either direction between adjustments so that long-term implantation is realized.

As an advantageous approach to reducing the necessary size of the infuser device 20 is to utilize TET for powering actuation and control circuitry from the external portion 13. Telemetry relays the amount of fluid in the infuser device 20 to the external assembly 13 for display, and in some applications for closing the loop on volume adjustment. To that end, the external system 13 may include a primary coil 24 positioned outside of the patient proximally placed to the infuser device 20 that is inside of the patient to inductively couple with a secondary coil (not shown) located within the infuser device 20. A programmer 26, which is connected via electrical cabling 28 to the primary coil 24, activates and monitors the primary coil 24.

Efficient power coupling of primary and secondary TET coils is described in five co-pending and co-owned patent applications filed on Jun. 24, 2004, all of which are hereby incorporated by reference in their entirety, (1) "TRANSCUTANEOUS ENERGY TRANSFER PRIMARY COIL WITH A HIGH ASPECT FERRITE CORE" to James Giordano, Daniel F. Dlugos, Jr. & William L. Hassler, Jr., Ser. No. 10/876307; (2) "MEDICAL IMPLANT HAVING CLOSED LOOP TRANSCUTANEOUS ENERGY TRANSFER (TET) POWER TRANSFER REGULATION CIRCUITRY" to William L. Hassler, Jr., Ed Bloom, Ser. No. 10/876038; (3) "SPATIALLY DECOUPLED TWIN SECONDARY COILS FOR OPTIMIZING TRANSCUTANEOUS ENERGY TRANSFER (TET) POWER TRANSFER CHARACTERISTICS" to Resha H. Desai, William L. Hassler, Jr., Ser. No. 10/876057; (4) "LOW FREQUENCY TRANSCUTANEOUS TELEMETRY TO IMPLANTED MEDICAL DEVICE" to William L. Hassler, Jr., Ser. No. 10/876058; and (5) "LOW FREQUENCY TRANSCUTANEOUS ENERGY TRANSFER TO IMPLANTED MEDICAL DEVICE" to William L. Hassler, Jr., Daniel F. Dlugos, Jr., Ser. No. 10/876307.

Figure 2:
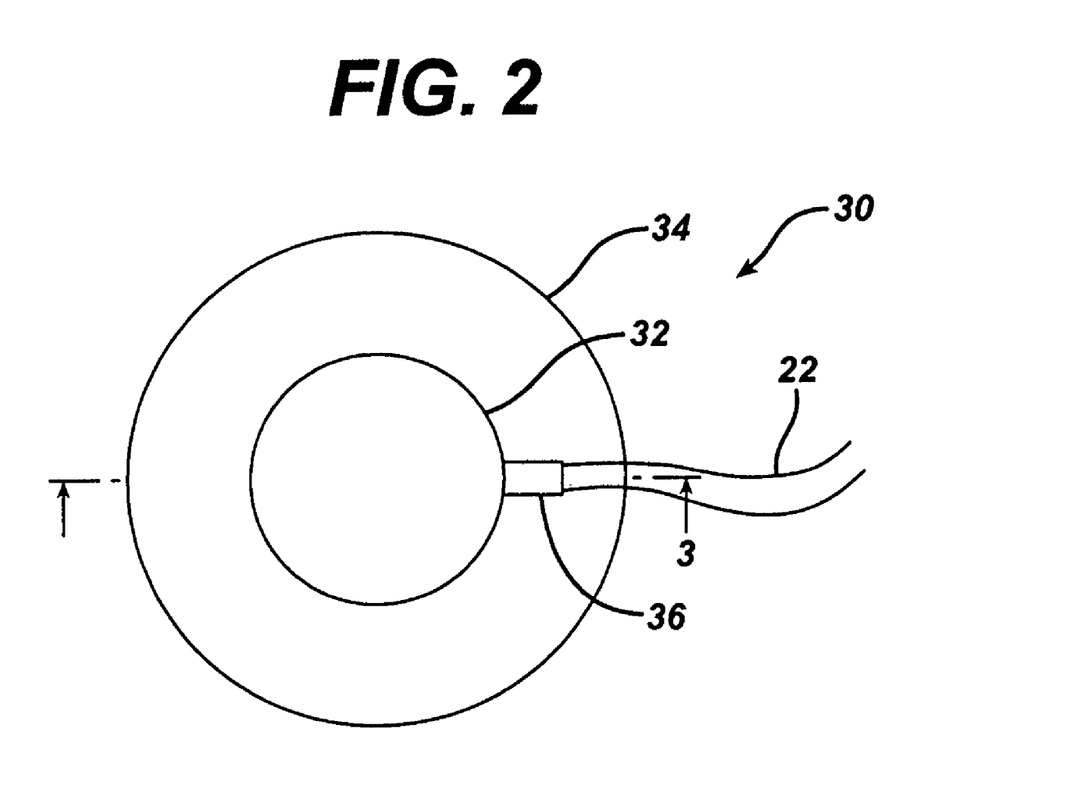
FIG. 2 is a top plan view of a bi-directional infuser device of the adjustable artificial sphincter system of FIG. 1.
Figure 3:
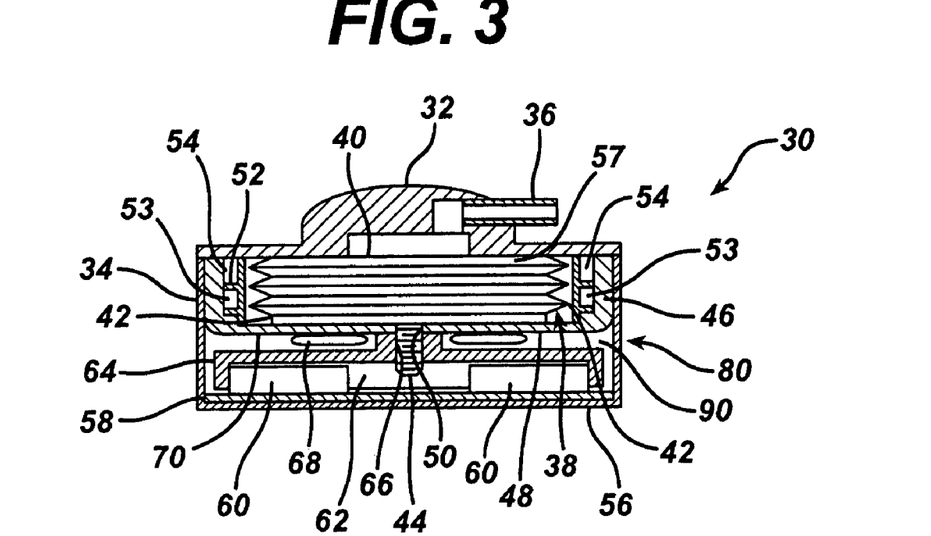
FIG. 3 is a sectioned side elevation view of the infuser device of FIG. 2, taken along section line 3-3, showing a version of a bellows accumulator position sensor based on variable inductance, and showing a bellows in an extended position.
Figure 4:
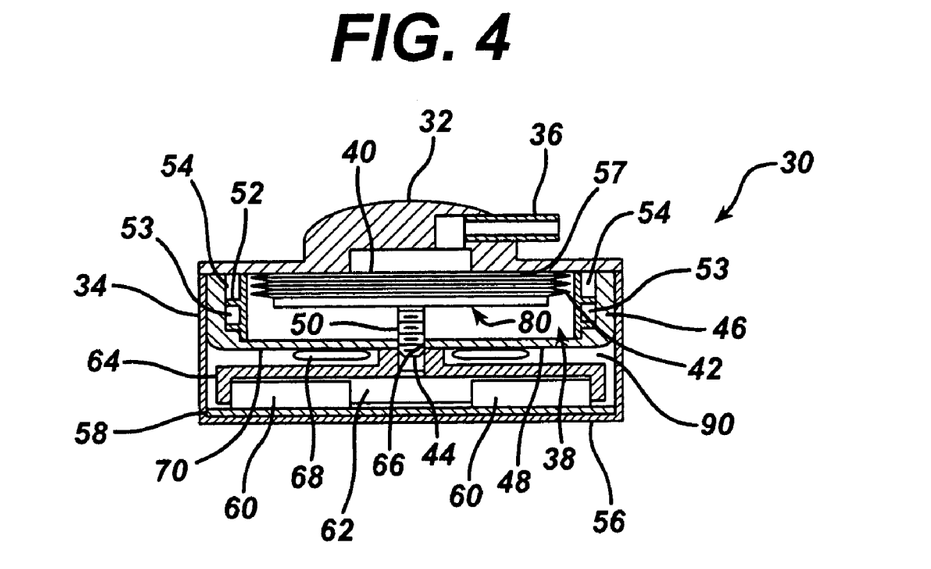
FIG. 4 is a sectioned side elevation view of the infuser device of FIG. 2, similar to FIG. 2, but showing a bellows in a collapsed position.

With reference to FIGS. 2-4, an implantable infuser device 30 incorporates inductive volume sensing. Infuser device 30 includes a fluid discharge head 32 and a cylindrical outer casing 34 sealed hermetically thereto, such as by welding. Discharge head 32 has a discharge conduit 36 sealably attached thereto and in fluid communication with a cylindrical bellows fluid accumulator ("bellows") 38. Bellows 38 has an open (fixed) end 40 welded to an inner surface of discharge head 32. Bellows 38 also has a closed (moving) end 42 fixedly attached to a lead screw 44 centered at the longitudinal axis of bellows 38 and extending away from bellows 38. Lead screw 44 has fine male threads such as ¼"-32 thereon.

Connected to and extending from discharge head 32 surrounding the circumference of bellows 38 is a cylindrical member 46 having a rigid bottom surface 48 and a clearance hole 50 centered therein through which lead screw 44 passes. Press-fit inside cylindrical member 46 and outside the perimeter of bellows 38 is a cylindrical bobbin 52 for housing spaced-apart secondary telemetry and transcutaneous energy transfer wire coils (not shown) in annular coil cavities 53, 54 formed with the cylindrical member 46, for receiving an actuation signal and induced power respectively from outside the patient's body to operate the infuser device 30.

Cylindrical outer casing 34 has a base 56 substantially parallel to the inner surface 57 of discharge head 32. Fixedly attached to this base 56 is control circuitry, depicted as a circuit board 58, which contains a microprocessor and other electronic devices for operating the infuser device 30. Attached to circuit board 58 are two piezoelectric motors 60 symmetrically spaced about lead screw 44, having drive mechanisms frictionally contacting an inner rim 62 of a disk 64 centered about lead screw 44. Disk 64 has an internally threaded boss 66 extending therefrom toward bellows 38. Threaded boss 66 has matching ¼"-32 threads, which accurately mate with threads of lead screw 44 to form a nut which when rotated with disk 64 by motors 60 about lead screw 44, drive lead screw 44 and bellows 38 axially to expand or collapse the bellows 38. Motors 60 and TET/telemetry coils (not shown) are electrically connected to circuit board 58, all contained within outer casing 34.

It is desirable to sense the extended or collapsed position of bellows 38 to closed-loop control that position in order to accurately transfer a desired volume of fluid to and from the bellows 38. To that end, a pancake inductance coil 68 is placed in fixed position parallel to and axially aligned with closed end 42 of bellows 38. Coil 68 is preferably attached to a rigid bottom surface 70 of cylindrical member 46, for example, to minimize the distance between the coil 68 and the closed end 42 of the bellows 38. A parallel tuned tank circuit on circuit board 58, commonly known in the electronic controls art, oscillates at a frequency of resonance depending on the number and diameter of turns in inductance coil 68, the electrical capacitance in parallel with coil 68, and the closeness of closed end 42 to coil 68, forming an inductive position sensor 80. In the illustrative version, inductance coil 68 is a spiral shaped coil of about 200 turns made of 40 gauge copper wire. A microprocessor on the circuit board 58 measures the frequency of oscillation and compares it to a table of frequencies in order to provide an error signal to indicate how close the actual bellows position is to the command position desired. Piezoelectric motors 60, combined with driven disk 64 and threaded boss 66, actuate the bellows 38 via lead screw 44, forming a bellows actuators 90.

It should be appreciated that a position sensor that is not dependent upon the presence and/or rotation of a lead screw such as the afore-described inductive position sensor may have application in an infuser device that is thermodynamically actuated, such as described in the afore-mentioned cross-referenced applications.

Figure 5:
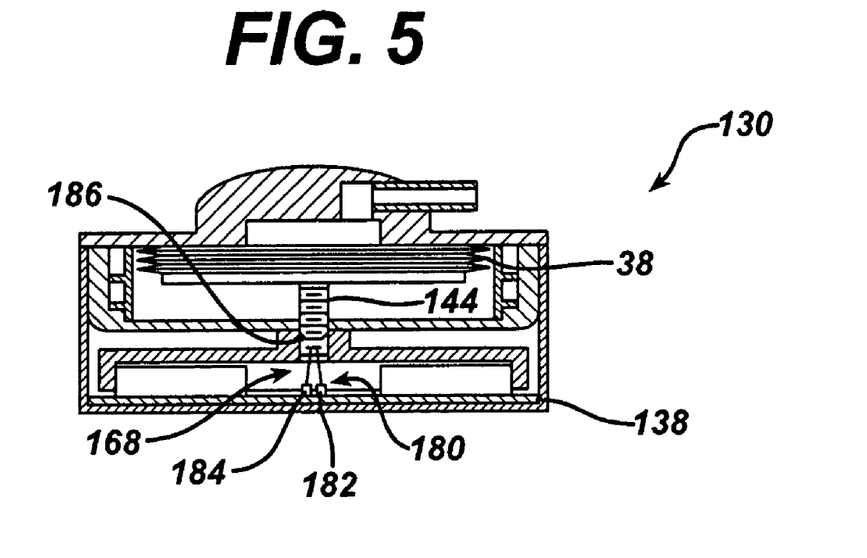
FIG. 5 is a sectioned side elevation view of the infuser device of FIG. 2, taken along section line 3-3, showing a second version of a bellows accumulator position sensor based on optical sensing based on reflectance from a lead screw varying with distance, and showing a bellows in a collapsed position.

In FIG. 5, an infuser device 130 has identical components to the infuser device 30 of FIGS. 2-4 with the exception of using optical position sensing of the bellows 38. In particular, instead of an inductance coil, position sensing, and thus volume sensing, is alternatively accomplished by an optical sensor 168. A light emitting diode (LED) 182 is shown mounted to a circuit board 138 beside a photodiode 184, also mounted to the circuit board 138. Both LED 182 and photodiode 184 are positioned near the axis of a lead screw 134 so that LED 182 emits light that is reflected by a distal end 186 of lead screw 144 toward photodiode 184. Since the LED 182 emits noncolumnated light, the distance of the distal end of the lead screw 144 from the photodiode 184 is inversely related to the amount of light from the LED 182 reflected from the lead screw 144 that is collected by the photodiode 184. A distal end 186 of the lead screw 144 may include surface treatment or shaping to provide a monotonic amount of reflected light as a function of distance, accommodating for instance an offset from the axis of the lead screw 144 of the LED 182 and/or the photodiode 184. The LED 182 and photodiode 184 and distal end 186 of lead screw 134 form position sensor 180. Photodiode 184 and LED 182 components are ubiquitous in many forms and performance. Many different ones and combinations of them can be successfully utilized in this application by one skilled in the control art.

Figure 6:
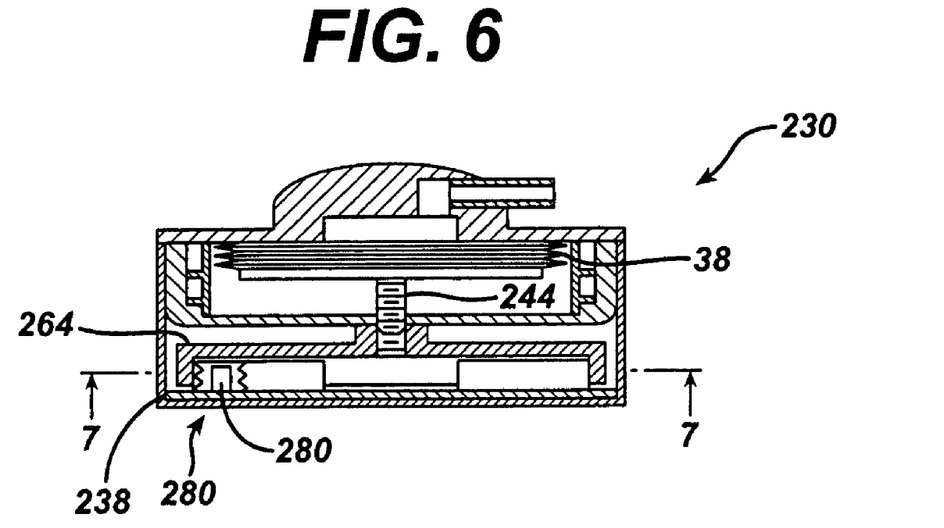
FIG. 6 is a sectioned side elevation view of the housing of FIG. 1, taken along section line 2-2, showing a third version of a bellows accumulator position sensor based upon absolute optical angular encoding, and showing a bellows in a collapsed position.
Figure 7:
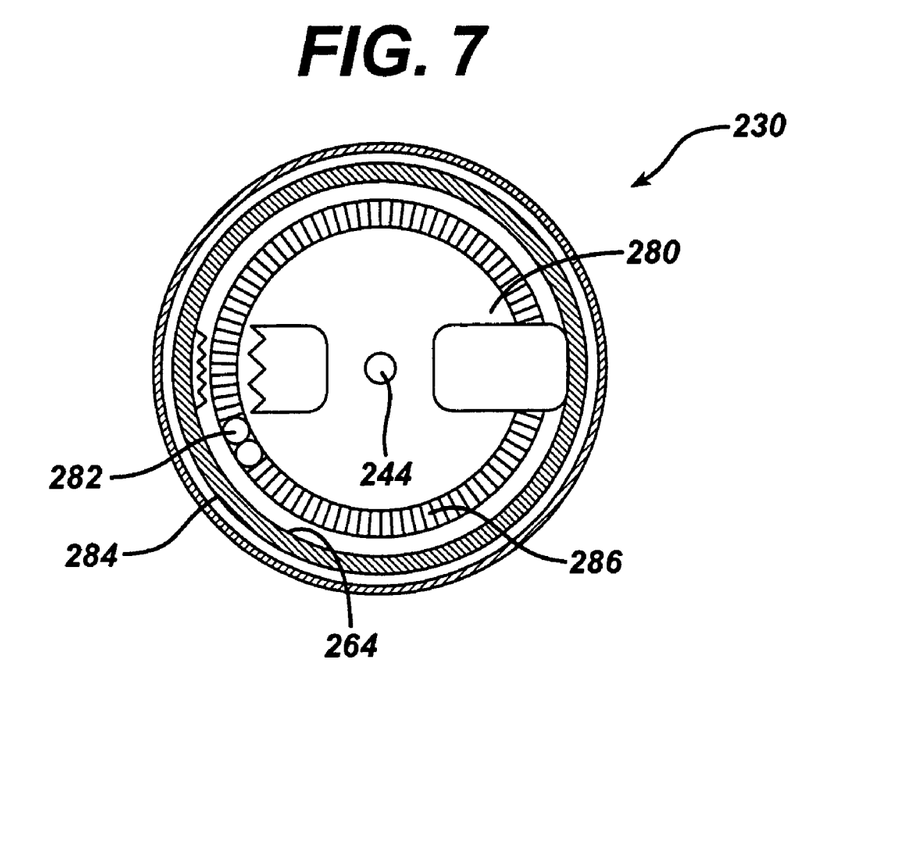
FIG. 7 is a sectioned bottom plan view of FIG. 6, taken along section line 7-7, showing an encoding ring on the underside of the driven disk and a single scanner to read absolute angular displacement therefrom.

In FIGS. 6 and 7, an infuser device 230 has identical components as infuser device 30 but incorporates an angular optical position sensor, depicted as an optical encoder 280. In particular, instead of LED 182 and photodiode 184 aimed at the lead screw 144, a LED 282 and photodiode 284 are mounted to a circuit board 238 and are located near an inner rim 242 of a rotatable disk 244. On the side of disk 264 facing circuit board 238 is printed a circular pattern of radial lines 286 having high contrast with their background. LED 282 and photodiode 284 form a scanner 288, which senses the position of the circular pattern of radial lines 286. When disk 264 rotates to move a lead screw 234, scanner 288 signals an encoder portion of circuit board 238 a count of lines 286 which have passed by. The count of lines 286 is directly proportional to movement of lead screw 244 and therefore of the bellows 38.

In another version of the scanner and lines embodiment of angular optical position sensor 280, a second scanner, not shown, is placed at 90 degrees out of phase with respect to the encoding pattern 286 and to scanner 288 to form a quadrature form of encoding, commonly known in the control art, which enables the encoder 280 to sense both position and direction of disk rotation. In yet another version, a gray scale, not shown but commonly known in the encoding art, replaces the simple radial line pattern. The gray scale establishes absolute position of the rotatable disk 264 because each position of the gray scale provides a unique signature.

Figure 8:
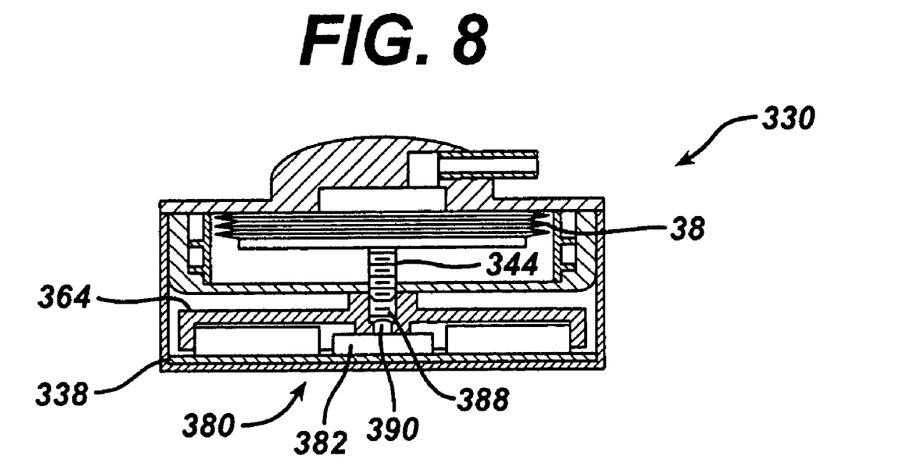
FIG. 8 is a sectioned side elevation view of the housing of FIG. 2, taken along section line 2-2, showing a fourth version of a bellows accumulator position sensor based upon a potentiometer, and showing a bellows in a collapsed position.

In FIG. 8, an infuser device 330 has identical components as infuser device 30 but incorporates angular resistance position sensor 380 instead of an inductive, linear optical, or angular optical position sensor 80, 180, 280. Instead of LED and photodiode reflectance or scanners, and instead of an inductance coil, position sensing is achieved by a potentiometer 382. A rotatable disk 364 has a boss extension 388 that is fixedly connected to a shaft 390 of the potentiometer 382 whose body is mounted to a circuit board 338. When disk 364 is rotated to drive a lead screw 344, shaft 390 of the potentiometer 382 is rotated. Such rotation is directly proportional to the movement of lead screw 344 and therefore of the bellows 38. Thus, bellows position control is achieved in this alternative by measuring the resistance within the potentiometer 382 and comparing that resistance with a table of resistances in the microprocessor of the circuit board 338. The table of resistances in the microprocessor is part of the control algorithm 54. Potentiometer components are ubiquitous in very many forms, and performance. Many different ones and combinations of them can be successfully utilized in this application by one skilled in the control art.

Figure 9:
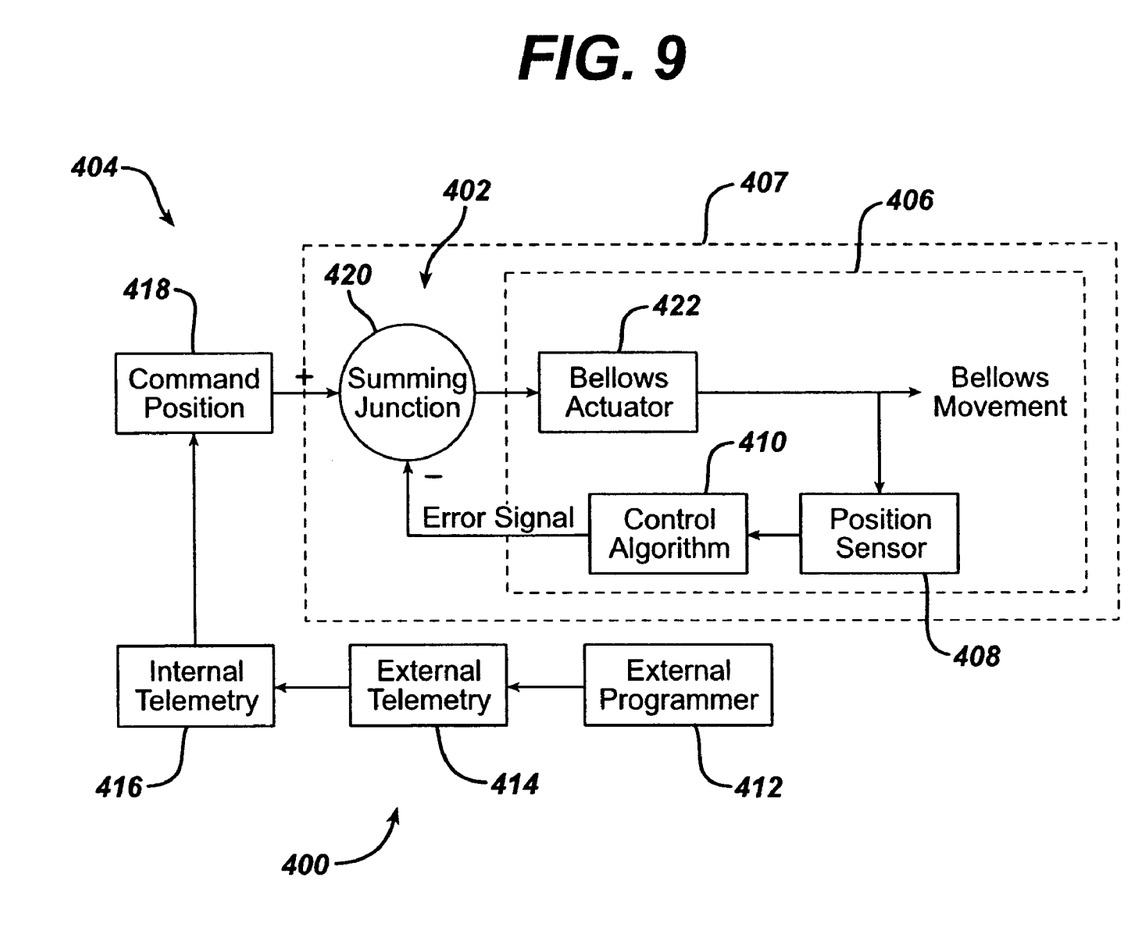
FIG. 9 is a block diagram of closed loop control of an artificial sphincter system for collapsing and extending the bellows accumulator.

In FIG. 9, a control system 400 performs closed-loop volume feedback in order to accurately adjust and maintain hydraulic volume in the adjustable gastric band 18 of FIG. 1. In the illustrative version, this control system 400 includes an inner control loop 402 performed by the infuser device 30, 130, 230, 330 (not shown in FIG. 9) to accurately adjust to a desired volume. In the illustrative version, the infuser device 30, 130, 230, 330 is TET powered as well as receiving telemetry commands from an outer control loop 404. It should be appreciated that the inner control loop 402 may be closed outside of the infuser device 30, 130, 230, 330, as depicted by the smaller box 406, as described above. In the illustrative version, however, the infuser device 30, 130, 230, 330 closes the inner control loop 402, as depicted by box 407 utilizing position sensing (block 408) that is responsive to bellows movement. A control algorithm 410 converts the sensed position value into a calculated error signal.

An external portion of the control system 400 is provided by an external programmer 412 that selects a volume for adjusting the artificial sphincter and transmits this position command from an external (primary) telemetry circuit 414 to an internal (secondary) telemetry circuit 416 that is converted to a command position value 418. Differential summing of the command position value 420 and the error signal results in bellows actuator drive command 422 that results in a bellows movement that is sensed as part of the iterative, closed-loop control of volume adjustment.

In the version with an inductive position sensor 80, the table of frequencies in the microprocessor is part of the control algorithm 410. In the linear optical position sensor 180, bellows position control is achieved by measuring the amount of reflected light at the photodiode 184 and comparing that with a table of light levels in the microprocessor. The table of light levels in the microprocessor is part of the control algorithm 410. The control algorithm 410 modifies the error signal in order to eliminate the difference between the actual bellows position and the command bellows position 418. This error signal modification can be as simple as using a Proportional, Integral, and Differential (PID) control law. This control law, commonly known in the control art, takes the original error signal and multiplies it by a fixed proportional gain constant, and then adds it to the integration of the original error signal with respect to time multiplied by an integral gain constant, and then this sum is added to the time derivative of the original error signal multiplied by a deferential gain constant to form the final error signal to be summed with the command signal. By adjusting or tuning these three different gain constants, the position error signal can be optimized for smoothest and quickest response over the bellows range of travel.

In a version with an angular optical sensor 280, bellows position is sensed in this alternative by measuring the count of lines passing the scanner and comparing that count with a table of line counts in the microprocessor of circuit board 238 to establish an error signal in the control system illustrated in FIG. 9. The table of line counts in the microprocessor is the control algorithm 410. The scanner 288 and lines 286 form position sensor 280. Scanning components are ubiquitous in very many forms, and performance. Many different ones and combinations of them can be successfully utilized in this application by one skilled in the control art.

While preferred embodiments of the present invention have been shown and described herein, it will be obvious to those skilled in the art that such embodiments are provided by way of example only. Numerous variations, changes, and substitutions will now occur to those skilled in the art without departing from the invention. In addition, it should be understood that every structure described above has a function and such structure can be referred to as a means for performing that function.

For example, it will become readily apparent to those skilled in the art that the above invention has equal applicability to other types of implantable bands. For example, bands are used for the treatment of fecal incontinence. One such band is described in U.S. Pat. No. 6,461,292, which is hereby incorporated herein by reference. Bands can also be used to treat urinary incontinence. One such band is described in U.S. patent application 2003/0105385, which is hereby incorporated herein by reference. Bands can also be used to treat heartburn and/or acid reflux. One such band is described in U.S. Pat. No. 6,470,892, which is hereby incorporated herein by reference. Bands can also be used to treat impotence. One such band is described in U.S. patent application No. 2003/0114729, which is hereby incorporated herein by reference.

For another example, while microprocessor closed-loop control with position conversion lookup tables is described, various other forms of computational circuitry may be used to perform closed-loop control, such as operational amplifier filter circuits, a state machine, a neural network, lumped component analog control circuitry, etc.

For an additional example, while a cylindrical titanium bellows accumulator with accordion-like sides is illustrated herein, it should be appreciated that other shapes of accumulators and other materials may be used consistent with aspects of the invention. For example, forming a sidewall of a resilient material may advantageously achieve greater displaceable volume, allowing further reduction in the size of an implant.

Accordingly, it is intended that the invention be limited only by the spirit and scope of the appended claims.

What is claimed is:

1. A method for remotely hydraulically controlling a hydraulically actuated therapeutic member, the method comprising:
   providing a hydraulically actuated therapeutic device;
   providing an implantable infuser device, the implantable infuser device comprising:
      an accumulator in fluid communication with the hydraulically actuated therapeutic device and having a surface movable to vary a contained volume between a first volume and a second volume,
      an induction position sensor inductively coupled to the movable surface of the accumulator and operably configured to sense an absolute position value,
      a closed loop controller responsive to a target volume value and the absolute position value to position the movable surface of the accumulator to the target volume value, and
      an enclosure encompassing the accumulator, wherein the position sensor comprises an inductive position sensor including an inductive target coupled for movement with the movable surface of the accumulator and an inductive coil attached to an internal surface of the enclosure proximate to the inductive target;
   transmitting a command to the infuser device to cause a change of volume of the accumulator of the infuser device to shift fluid between the infuser device and the hydraulically actuated therapeutic device;
   sensing accumulator position;
   calculating an error signal based upon a commanded volume and a current volume related to the sensed accumulator position; and
   commanding an actuator to change accumulator position based upon the calculated error signal.

2. The method of claim 1, wherein the hydraulically actuated therapeutic device comprises an artificial sphincter encircling a bodily lumen, the method further comprising:
   transmitting the command to the infuser device to cause a change of volume of the accumulator to shift fluid between the infuser device and the artificial sphincter encircling a bodily lumen.

3. The method of claim 1, further comprising:
   providing transcutaneous energy transfer power to the infuser device.

4. An implantable infuser device for hydraulically actuating an implanted therapeutic device, the implantable infuser device comprising:
   an accumulator having a surface that is movable between a first and second position to selectively vary a contained fluid volume;
   a position sensor coupled to the movable surface of the accumulator and operably configured to sense an absolute position value;
   a closed loop controller responsive to a target volume value and the absolute position value to position the movable surface of the accumulator to the target volume value: and
   an enclosure encompassing the accumulator, wherein the position sensor comprises an inductive position sensor including an inductive target coupled for movement with the movable surface of the accumulator and an inductive coil attached to an internal surface of the enclosure proximate to the inductive target.

5. The implantable infuser device of claim 4, wherein the inductive position sensor further comprises computation circuitry operably configured to relate a sensed value from the inductive position sensor to the absolute position value.

6. The implantable infuser device of claim 4, further comprising:
   a transmission forming a lead screw engagement with the enclosure and operably coupled to exert a selectively positive and negative displacement force upon the movable surface of the accumulator; and an actuator operably configured to rotate the transmission.

7. An apparatus, comprising:
   a hydraulically actuated therapeutic device comprising a fluid bladder; and an implantable infuser device comprising:
      an accumulator in fluid communication with the fluid bladder and having a surface movable to vary a contained volume between a first volume and a second volume,
      an inductive position sensor coupled to the movable surface of the accumulator and operably configured to sense an absolute position value, wherein the inductive position sensor further comprises computation circuitry operably configured to relate a sensed value from the inductive position sensor to the absolute position value, and
      a closed loop controller responsive to a target volume value and the absolute position value to position the movable surface of the accumulator to the target volume value.

8. The apparatus of claim 7, further comprising a transcutaneous energy transfer system including an external portion including a programmer and primary coil and an implantable internal portion including a secondary coil in electrical communication with the closed loop controller.

9. The apparatus of claim 7, wherein the implantable infuser device further comprises an enclosure encompassing the accumulator, wherein the position sensor comprises an inductive position sensor including an inductive target coupled for movement with the movable surface of the accumulator and an inductive coil attached to an internal surface of the enclosure proximate to the inductive target.

10. The apparatus of claim 7, wherein the implantable infuser device further comprises:

an enclosure;

a transmission forming a lead screw engagement with the enclosure and operably coupled to exert a selectively positive and negative displacement force upon the movable surface of the accumulator; and an actuator operably configured to rotate the transmission.

11. The apparatus of claim 10, wherein the position sensor further comprises a means for actuating the accumulator.

12. The apparatus of claim 7, wherein the hydraulically actuated therapeutic membef device comprises an implantable band operably configured to encircle a bodily lumen of a patient and including an inwardly directed fluid bladder for adjusting an inner diameter.

* * * * *